United States Patent
Kuhn et al.

(10) Patent No.: US 6,680,404 B1
(45) Date of Patent: Jan. 20, 2004

(54) METHOD OF PRODUCING ALKOXYCINNAMIC ACID ESTER

(75) Inventors: Walter Kuhn, Holzminden (DE); Werner Marks, Brevörde (DE); Klaus Zahlmann, Holzminden (DE)

(73) Assignee: Symrise GmbH & Co. KG (DE)

( * ) Notice: Subject to any disclaimer, the term of this patent is extended or adjusted under 35 U.S.C. 154(b) by 0 days.

(21) Appl. No.: 09/979,440

(22) PCT Filed: May 16, 2000

(86) PCT No.: PCT/EP00/04421

§ 371 (c)(1),
(2), (4) Date: Nov. 16, 2001

(87) PCT Pub. No.: WO00/73255

PCT Pub. Date: Dec. 7, 2000

(30) Foreign Application Priority Data

May 27, 1999 (DE) .......................................... 199 24 402
May 9, 2000 (DE) .......................................... 100 22 108

(51) Int. Cl.$^7$ ................................................ C07C 69/76
(52) U.S. Cl. ........................................................ 560/55
(58) Field of Search ........................................... 560/55

(56) References Cited

U.S. PATENT DOCUMENTS 4,765,977 A * 8/1988 Baron
5,527,947 A 6/1996 Alexander et al. ............ 560/55

OTHER PUBLICATIONS

Zhaona, S et al Huaxue Shiji (2002) 24(5) 307–308.*

* cited by examiner

Primary Examiner—Paul J. Killos
(74) Attorney, Agent, or Firm—Pendorf & Cutliff

(57) ABSTRACT

The invention relates to a method of producing alkoxycinnamic acid ester (alkoxy cinnamate) by condensing $C_5$–$C_8$ acetic acid esters with $C_1$–$C_4$ alkoxybenzaldehyde in the presence of an alkaline and/or alkaline earth $C_1$–$C_4$ alcoholate and removing the $C_1$–$C_4$ alcohol that is produced by this reaction from the reaction mixture.

20 Claims, No Drawings

METHOD OF PRODUCING ALKOXYCINNAMIC ACID ESTER

FIELD OF THE INVENTION

The invention relates to the preparation of alkoxycinnamic esters (alkoxycinnamates).

BACKGROUND OF THE INVENTION

2-Ethylhexyl 4-methoxycinnamate and 3-methylbutyl 4-methoxycinnamate and isomers thereof are known and efficient light protection agents for the UV-B region and are prepared on an industrial scale.

To prepare these products, processes are sought which are low-cost and can be carried out with large yields.

U.S. Pat. No. 5,527,947 describes a process in which $C_1$–$C_4$-alkoxybenzaldehydes, such as anisaldehyde, and $C_1$–$C_4$-alkyl acetates, such as methyl acetate, are dissolved in an inert hydrocarbon, such as heptane, toluene or petroleum ether. In the presence of a strongly alkaline metal base, such as sodium methoxide, the feed substances react to give a mixture of the corresponding $C_1$–$C_4$-alkyl-$C_1$–$C_4$-alkoxy cinnamates, the alkali metal salts of the corresponding $C_1$–$C_4$-alkoxy cinnamic acid and the $C_1$–$C_4$-alkanols. Following acidification of the reaction mixture with a strong polybasic acid, such as sulfuric acid, the liberated acetic acid is esterified with the $C_1$–$C_4$-alkanoles and distilled off. The mixture of $C_1$–$C_4$-alkyl-$C_1$–$C_4$-alkoxycinnamates and $C_1$–$C_4$-alkoxycinnamic acids which remains is reacted with a $C_5$–$C_{14}$-alkanol in the presence of a metal salt of a strong polybasic acid, such as sulfuric acid. Following transesterification and esterification, the corresponding $C_5$–$C_{14}$-alkyl-$C_1$–$C_4$-alkoxycinnamate, e.g. 2-ethylhexyl-4-methoxycinnamate, is obtained with 83 to 87% yield.

SUMMARY OF THE INVENTION

We have found a process for the preparation of cinnamic esters of the formula

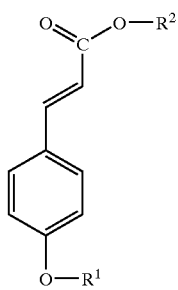

in which
$R^1$ is an alkyl group having 1 to 4 carbon atoms and
$R^2$ is 2-ethylhexyl or 3-methylbutyl,
which comprises condensing acetic $C_5$–$C_8$-esters of the formula

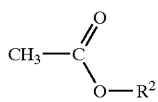

in which $R^2$ has the meaning given above,
with an alkoxybenzaldehyde of the formula

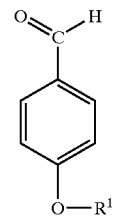

in which $R^1$ has the meaning given above,
in the presence of an alkali metal alkoxide, and removing alcohol which form during the reaction.

DETAILED DESCRIPTION OF THE INVENTION

The process according to the invention can be illustrated by the following equation:

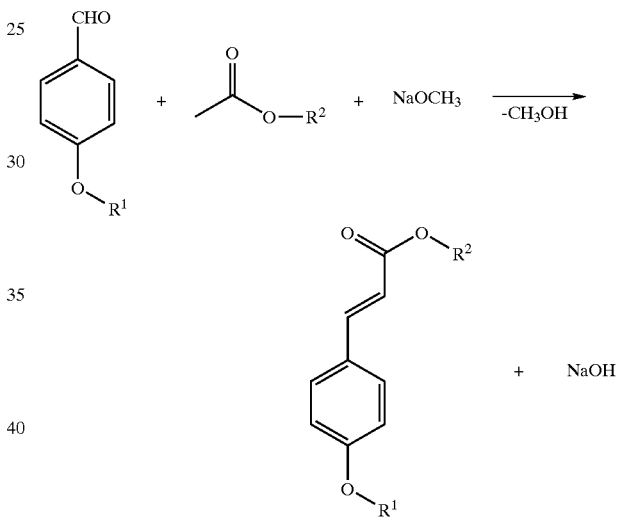

Alkoxybenzaldehydes for the process according to the invention may, for example, be anisaldehyde, 4-ethoxybenzaldehyde, 4-propoxybenzaldehyde, 4-isopropoxy-benzaldehyde, 4-butoxybenzaldehyde and 4-isobutoxybenzaldehyde.

The acetic $C_5$–$C_8$-esters for the process according to the invention are 2-ethylhexyl acetate or 3-methylbutyl acetate.

Alkali metal alkoxides for the process according to the invention are preferably the sodium and potassium alkoxides of lower aliphatic alcohols ($C_1$ to about $C_4$), such as methanol, ethanol, propanol, isopropanol, butanol and isobutanol. Particular preference is given to sodium methoxide.

The acetic $C_5$–$C_8$-esters can be used in pure form or in a mixture with 2-ethylhexanol or 3-methylbutanol. In order to increase the economic feasibility of the process, it is advantageous to prepare 2-ethylhexyl acetate or 3-methylbutyl acetate before or during the condensation reaction in situ, and to use this reaction mixture without purification or washing for the condensation reaction.

This may be carried out, for example, by a) transesterifying 2-ethylhexanol or 3-methylbutanol with an acetic $C_1$–$C_4$-ester, such as methyl acetate, ethyl acetate, propyl acetate, isopropyl acetate, butyl acetate or isobutyl acetate, in the presence of an alkali metal alkoxide and/or alkaline earth metal alkoxide to give the feed material 2-ethylhexyl acetate or 3-methylbutyl acetate, or b) esterifying 2-ethylhexanol or 3-methylbutanol with acetic acid autocatalytically or in the presence of catalytic amounts of a strong acid, such as sulfuric acid or 4-toluenesulfonic acid, and subjecting the mixture to incipient distillation.

The mixture prepared under a) can immediately be taken with a $C_1$–$C_4$-alkoxybenzaldehyde, such as anisaldehyde, to the condensation reaction.

The mixture prepared under b) is prepared for the condensation reaction by adding alkali metal alkoxide.

The alkoxybenzaldehyde is preferably added in the temperature range from −10 to 120° C., particularly preferably from 10 to 30° C., over the course of from 0.5 to 5 hours, particularly preferably 1 to 2 hours.

After-stirring is carried out for 0.5 to 10 hours, preferably 1 to 3 hours, the reaction temperature being increased to 50 to 150° C., preferably 80 to 110° C. During the after-stirring, a vacuum of from 800 mbar to 2 mbar, preferably from 80 mbar to 40 mbar, is applied.

The alcohol which forms during the process according to the invention is preferably separated off during distillation in a vacuum.

In the after-stirring period under vacuum, residual alkoxybenzaldehyde is reacted to give the 4-alkoxycinnamic ester, and lower homologous 4-methoxycinnamates are transesterified to give the alkoxycinnamic ester according to the invention, 2-ethylhexyl 4-methoxycinnamate or 3-methylbutyl 4-methoxycinnamate.

The reaction mixture is then preferably admixed with a strong acid, such as sulfuric acid, sulfuric acid/NaHSO$_4$ or 4-toluenesulfonic acid. The mixture is then distilled up to a bottom temperature of 150° C., the 4-methoxycinnamic acid (about 20%) which forms as byproduct being esterified to give the alkoxycinnamic ester according to the invention. At the same time, acetic acid which has formed is esterified to give 2-ethylhexyl acetate or 3-methylbutyl acetate. After washing and distillation, 2-ethylhexyl 4-methoxycinnamate or 3-methylbutyl 4-methoxycinnamate is obtained with high yield (90 to 93%) and high purity (96 to 98%) in a simple distillation.

The intermediate fractions 2-ethylhexanol/2-ethylhexyl acetate or 3-methylbutanol/3-methylbutyl acetate which form during the distillation can be co-used again in the next condensation reaction.

The advantages of the process according to the invention are:

Use of low-cost raw materials

Minimizing of waste materials and reuse of secondary streams

Minimizing of organic contaminants in waste water

It is surprising that alkoxycinnamic esters can be prepared by the process according to the invention in high yields and in high purity by simple distillation.

EXAMPLES

Preparation of 2-ethylhexyl 4-methoxycinnamate

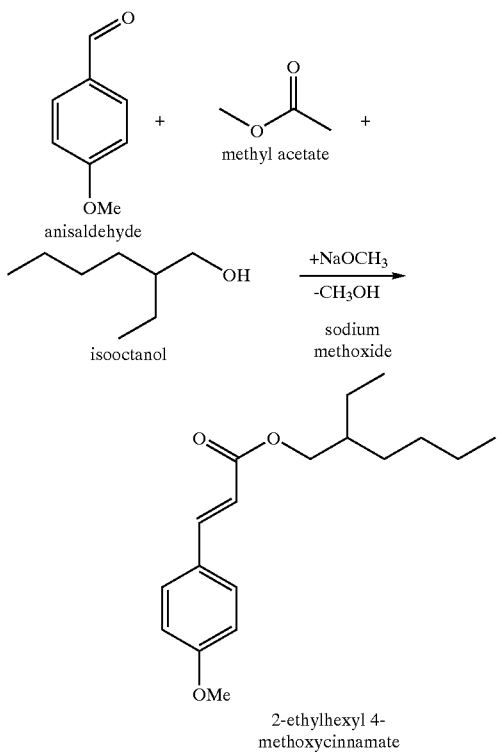

2-ethylhexyl 4-methoxycinnamate

Example 1

H$_2$SO$_4$/NaHSO$_4$ Variant

A 6 l jacketed vessel is charged with 2 106 g of 2-ethylhexanol=16.20 mol 1 200 g of methyl acetate=16.20 mol 187 g of sodium methoxide=3.46 mol At 20 to 30° C., 440.0 g of anisaldehyde=3.24 mol are metered in over about 80 minutes. The mixture is then heated to 100° C., a mixture of methanol and methyl acetate distilling off. As the distillation abates, a vacuum is applied at 60 mbar. At 100° C./60 mbar a total of approximately 920 g of low-boiling components are distilled off over 2 hours. For neutralization, 262 g of 70% strength sulfuric acid=1.87 mol are metered in at 100° C. over 15 minutes. Then, over 2 hours, approximately 160 g of water are removed azeotropically up to a bottom temperature of from 145 to 150° C. After cooling to <100° C., the mixture is washed with 700 g of water. Following phase separation, the mixture is after-washed with 200 g of water and 2 g of technical-grade sodium hydroxide solution. The organic phase is then distilled over a 10 cm Vigreux column.

| Fraction | Bottom temperature | Head temperature/ mbar | Weight |
|---|---|---|---|
| 1 | 67–200° C. | 52–125° C./2.5 | 1910 g (in each case 40–50% of 2-ethylhexanol/2-ethylhexyl acetate |

| Fraction | Bottom temperature | Head temperature/ mbar | Weight |
|---|---|---|---|
| 2 (Main Fraction) | –250° C. | –165° C./2.0 | 865 g (97% of 2-ethylhexyl 4-methoxycinnamate) |

The yield is 90% of theory.

Example 2

4-Toluenesulfonic Acid Variant

A 6 l jacketed vessel is charged with 2 106 g of 2-ethylhexanol 16.20 mol
1 200 g of methyl acetate=16.20 mol
187 g of sodium methoxide=3.46 mol At 20 to 30° C., 440 g of anisaldehyde=3.24 mol are metered in over about 80 minutes. The mixture is then heated to 100° C., a mixture of methanol and methyl acetate distilling off. As the distillation abates, a vacuum is applied at 60 mbar. At 100° C./60 mbar a total of approximately 920 g of low-boiling components are distilled off over 2 hours. For neutralization, 243 g of 70% strength sulfuric acid=1.73 mol (=equimolar amount) are metered in at 100° C. over 15 minutes. 20 g of 4-toluenesulfonic acid=3%, based on mol of Na methoxide, are added.

Further procedure as in Example 1.

| Fraction | Bottom temperature | Head temperature/ mbar | Weight |
|---|---|---|---|
| 1 | 64–195° C. | 51–111° C./15 | 1814 g (in each case 40–50% of 2-ethylhexanol/2-ethylhexyl acetate |
| 2 (Main Fraction) | –250° C. | –165° C./1.0 | 870 g (98% of 2-ethylhexyl 4-methoxycinnamate) |

The yield is 91.5% of theory.

Example 3

$H_2SO_4/NaHSO_4$ Variant With 2-Ethylhexanol/2-ethylhexyl Acetate Recycled

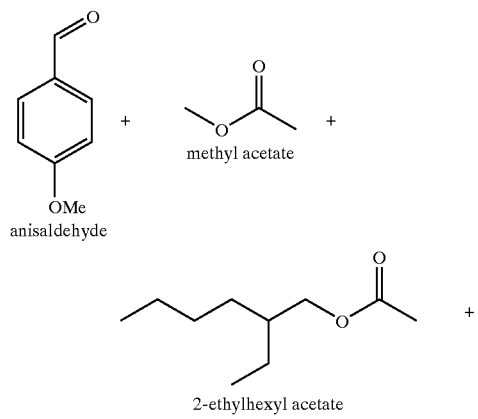

anisaldehyde + methyl acetate + 2-ethylhexyl acetate

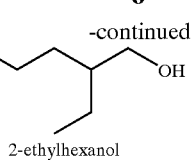

2-ethylhexanol

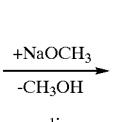

+NaOCH$_3$
-CH$_3$OH sodium methoxide

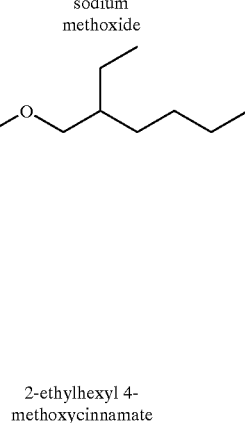

2-ethylhexyl 4-methoxycinnamate

A 6 l jacketed vessel is charged with 1685 g of 2-ethylhexanol/2-ethylhexyl acetate recycled consisting of 675 g=5.2 mol of 2-ethylhexanol and =5.9 mol of 2-ethylhexyl acetate)
480 g of 2-ethylhexanol=3.7 mol
720 g of methyl acetate=9.7 mol
187 g of sodium methoxide=3.46 mol.

At 20 to 30° C., 440 g of anisaldehyde=3.24 mol are metered in over about 80 minutes.

Further procedure analogous to Example 1, $H_2SO_4$ variant.

| Fraction | Bottom temperature | Head temperature/ mbar | Weight |
|---|---|---|---|
| 1 | 65–198° C. | 48–78° C./1.4–1.7 | 1700 g (38% of 2-ethylhexanol, 61% of 2-ethylhexyl acetate) |
| 2 (Main Fraction) | –265° C. | –170° C./1.6 | 906 g (96.1% of 2-ethylhexyl 4-methoxycinnamate) |

The yield is 92.7% of theory.

What is claimed is:

1. A process for the preparation of cinnamic esters of the formula

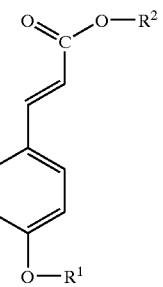

in which
  $R^1$ is an alkyl group having 1 to 4 carbon atoms and
  $R^2$ is 2-ethylhexyl or 3-methylbutyl,
  which comprises the steps of i) condensing acetic $C_5$–$C_8$-esters of the formula

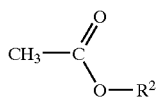

in which $R^2$ has the meaning given above,
with an alkoxybenzaldehyde of the formula

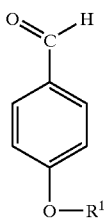

in which $R^1$ has the meaning given above,
in the presence of an alkali metal alkoxide, and
ii) removing alcohol which form during the reaction.

2. The process according to claim 1, wherein alkali metal alkoxides and/or alkaline earth metal alkoxides of lower alcohols are used.

3. The process according to claim 2, wherein the alkali metal alkoxide used is sodium methoxide.

4. The process according to claim 1, wherein the molar ratio of the reactants for the condensation acetic $C_5$–$C_8$-ester: alkoxybenzaldehyde: alkali metal alkoxide is 1.5 to 15:1:1.0 to 1.5.

5. The process according to claim 4, wherein the molar ratio of the reactants for the condensation acetic $C_5$–$C_8$-ester: alkoxybenzaldehyde: alkali metal alkoxide is approximately 5:1:1.1.

6. The process according to claim 1, wherein the condensation is carried out in the temperature range from 0 to 120° C.

7. The process according to claim 6, wherein the condensation is carried out in the temperature range from 10 to 30° C.

8. The process according to claim 1, wherein the condensation is carried out over the course of from 0.5 to 10 hours.

9. The process according to claim 8, wherein the condensation is carried out over the course of from 1 to 2 hours.

10. The process according to claim 1, wherein the alcohol which forms during the condensation is removed by a vacuum of from 800 mbar to 1 mbar.

11. The process according to claim 10, wherein the alcohol which forms during the condensation is removed by a vacuum of from 80 mbar to 40 mbar.

12. The process according to claim 1, wherein the acetic $C_5$–$C_8$-ester is prepared in situ.

13. The process according to claim 12, wherein the acetic $C_5$–$C_8$-ester is prepared in situ by reacting 2-ethylhexanol or 3-methylbutanol with acetic $C_1$–$C_4$-ester in the presence of an alkali metal alkoxide.

14. The process according to claim 1, wherein the acetic $C_5$–$C_8$-ester is prepared in situ by reacting 2-ethylhexanol or 3-methylbutanol with acetic acid autocatalytically or in the presence of catalytic amounts of a strong acid.

15. The process according to claim 14, wherein the strong acids used are sulfuric acid/$NaHSO_4$ or 4-toluenesulfonic acid.

16. The process according to claim 1, wherein the reaction product is reacted without isolation with the alkoxybenzaldehyde.

17. The process according to claim 1, wherein the acetic ester generated in situ is reacted without isolation with the alkoxide and then with the alkoxybenzaldehyde.

18. The process according to claim 1, wherein the condensation product is acidified with a strong acid, and the alkoxycinnamic acid which is present is esterified to form said alkoxycinnamic ester.

19. The process according to claim 1, wherein the ratio of the amount of strong acid to the alkoxide is 0.5 to 2:1.

20. The process according to claim 1, wherein the cinnamic esters are isolated from the reaction mixture by distillation.

* * * * *